United States Patent [19]

Denzinger et al.

[11] 4,200,710
[45] Apr. 29, 1980

[54] PREPARATION OF POLYVINYLPYRROLIDONE-IODINE

[75] Inventors: Walter Denzinger, Speyer; Hans-Uwe Schenck, Wachenheim; Wolfgang Schwarz, Ludwigshafen, all of Fed. Rep. of Germany

[73] Assignee: BASF Aktiengesellschaft, Fed. Rep. of Germany

[21] Appl. No.: 30,900

[22] Filed: Apr. 17, 1979

[30] Foreign Application Priority Data

Apr. 28, 1978 [DE] Fed. Rep. of Germany ....... 2818767

[51] Int. Cl.$^2$ .............................................. C08F 8/22
[52] U.S. Cl. ..................................... 525/356; 525/358
[58] Field of Search ........................................... 526/43

[56] References Cited

U.S. PATENT DOCUMENTS

| 2,706,701 | 4/1955 | Beller et al. | 167/70 |
|---|---|---|---|
| 2,754,245 | 7/1956 | Hosmer | 526/23 |
| 2,826,532 | 3/1958 | Hosmer | 167/70 |
| 2,900,305 | 8/1959 | Siggia | 167/70 |
| 3,028,300 | 4/1962 | Canter et al. | 167/17 |
| 3,136,755 | 6/1964 | Grosser et al. | 526/43 |
| 3,898,326 | 8/1975 | Canter et al. | 424/80 |
| 4,027,083 | 5/1977 | Herrle et al. | 526/23 |
| 4,157,433 | 6/1979 | Phillips | 526/43 |

*Primary Examiner*—William F. Hamrock
*Attorney, Agent, or Firm*—Keil & Witherspoon

[57] ABSTRACT

A process for the preparation of PVP-iodine by reacting polyvinylpyrrolidone powder with elementary iodine at from 70° to 100° C. The reaction is carried out in the presence of formic acid, oxalic acid or an ammonium salt or amide of carbonic acid, formic acid or oxalic acid. The process avoids the disadvantage of long periods of heating, which can result in degradation of the polyvinylpyrrolidone, and is particularly suitable for the preparation of a stable PVP-iodine using a low molecular weight polyvinylpyrrolidone.

4 Claims, No Drawings

PREPARATION OF POLYVINYLPYRROLIDONE-IODINE

The present invention relates to a process for the preparation of the reaction product of polyvinylpyrrolidone and elementary iodine, in general referred to as polyvinylpyrrolidone-iodine or, for brevity, PVP-iodine, which is increasingly being used for the sake of its germicidal, bactericidal, fungicidal and disinfectant properties.

PVP-iodine is generally marketed as a brown powder which contains about 11% of available iodine, ie. active iodine which can be titrated with sodium thiosulfate, and in addition contains about 5.5% of iodine in the form of the iodide. For an iodine-iodide ratio of 2:1, the iodine bond in the PVP-iodine complex is so strong that the odor of iodine is no longer perceptible and a moist potassium iodide/starch paper introduced into the gas space above the PVP-iodine no longer exhibits a coloration. In practice, the partition coefficient of the iodine between an aqueous PVP-iodine solution and heptane is used as a measure of satisfactorily firm bonding of the iodine; this coefficient, as described, for example, in U.S. Pat. No. 3,028,300, is about 200. Further, it is necessary that on storage the PVP-iodine formulation, in particular an aqueous solution of PVP-iodine, should lose very little available iodine, ie. the PVP-iodine should, in this form, be very stable.

A great variety of procedures for preparing a very stable PVP-iodine have been described. For example, according to German Pat. No. 1,037,075, the PVP-iodine powder is subjected to a prolonged heat treatment at 90°–100° C., whilst U.S. Pat. No. 2,900,305 proposes using a PVP having a defined moisture content for the preparation of a suitable PVP-iodine. U.S. Pat. No. 2,826,532 describes the addition of sodium bicarbonate and U.S. Pat. No. 3,028,300 the addition of an iodide in the form of hydriodic acid or an alkali metal iodide. U.S. Pat. No. 3,898,326 teaches adding hydrogen iodide or an alkali metal iodide to an aqueous PVP solution and reacting the pulverulent PVP-iodide mixture, obtained after drying the solution, with iodine. German Published Application DAS 2,439,197 describes a polyvinylpyrrolidone, obtained by polymerization in an anhydrous organic solvent, as particularly suitable for the preparation of a stable PVP-iodine.

The above prior art processes also aim to produce a stable PVP-iodine economically. However, they suffer from substantial disadvantages. Using the procedure described in German Pat. No. 1,037,075, heating at 90°–100° C. for from 18 to 64 hours is required to form the PVP-iodine complex if a stable product having an iodine:iodide ratio of 2:1 is to be obtained. The process described in U.S. Pat. No. 2,900,305 also as a rule requires 22 hours' heating. In the latter process, heating is additionally made difficult by the fact that, because of the requisite relatively high water content of 4–15% of the polyvinylpyrrolidone used, heating must in practice be carried out at below 90° C. to avoid caking of the mixture of polyvinylpyrrolidone and iodine, and hence even longer heating times become necessary than in the case of normal polyvinylpyrrolidone powder, which usually contains only up to 5% by weight of water.

According to the procedure of U.S. Pat. No. 3,028,300, heating is dispensed with by adding an iodide in the form of an alkali metal iodide or of hydriodic acid to the mixture of polyvinylpyrrolidone and iodine. This process again is not ideal, since inhomogeneous mixtures are produced, in which the iodine is only weakly bonded, so that the mixtures have a strong smell of iodine. Hence, U.S. Pat. No. 3,898,326 teaches adding iodides to an aqueous polyvinylpyrrolidone solution, which is subsequently dried, after which the pulverulent polyvinylpyrrolidone-iodide mixture is reacted with iodine without heat. If, in accordance with U.S. Pat. No. 3,898,326, the iodide is added as hydriodic acid to the polyvinylpyrrolidone, serious corrosion problems arise during drying, whilst if the iodide is added as an alkali metal iodide, the PVP-iodine no longer conforms to the stringent requirements of drug legislation because of the content of alkali metal in the product.

German Published Application DAS 2,439,197 also states that heating for 10 hours is the general rule, but in order to achieve partition coefficients of about 200 it is necessary to heat for at least 20 hours.

It is an object of the present invention to provide a process for the preparation of a PVP-iodine which is stable, particularly in its aqueous solutions, and has an iodine:iodide ratio of 2:1 and a partition coefficient of from 190 to 250, advantageously of about 200, which process avoids the known disadvantages, such as the long periods of heating. According to Defence Medical Purchase Description (No. 4, 1972) the loss of iodine of an aqueous PVP solution containing 1% of available iodine should be not more than 12% after 14 days' storage at 52° C. Of course, the PVP-iodine must also conform to the requirements of the pharmacopeias, such as those of United States Pharmacopeia XIX.

In particular, it is an object of the present invention to prepare a stable PVP-iodine with a low molecular weight polyvinylpyrrolidone having a K value of less than 20, which product can, according to the prior art, only be produced—because of the low softening point of the mixtures of the low molecular weight polyvinylpyrrolidone powder with iodine—with uneconomically long reaction times, which can result in degradation of the polymer, whilst the stability of the product as a rule is not entirely satisfactory.

We have found that this object is achieved, according to the invention, by preparing the PVP-iodine by mixing polyvinylpyrrolidone powder and iodine and then heating the mixture in the presence of a compound which accelerates the formation of iodide. Particularly suitable compounds for this purpose are those which, after the reaction with iodine, may, in addition to the iodide, form water and volatile substances, such as carbon dioxide or nitrogen.

Accordingly, the invention relates to a process for the preparation of a stable PVP-iodine by reacting PVP powder with elementary iodine at from 70° to 100° C., wherein the reaction is carried out in the presence of formic acid, oxalic acid or an ammonium salt or amide of carbonic acid, formic acid or oxalic acid.

Examples of compounds which accelerate the formation of iodide are, in addition to the acids mentioned, ammonium carbonate, ammonium bicarbonate, ammonium carbamate, urea, ammonium formate, formamide, ammonium oxalate, oxamic acid and oxamide.

Oxalic acid and formic acid, which, on reaction with iodine, only give carbon dioxide in addition to hydrogen iodide, are particularly preferred, as are their amides and ammonium salts.

The amount of the additive which accelerates the formation of iodide is as a rule selected so that on complete reaction from one-fifth to one-third of the iodine added to the polyvinylpyrrolidone powder is converted to iodide. Depending on the nature of the additive, this amount is from 2 to 30% by weight, preferably from 4 to 22% by weight, based on the iodine employed.

The additive which accelerates the formation of iodide is advantageously added directly when mixing the polyvinylpyrrolidone with the iodine in conventional powder mixers, for example tumbler mixers or double-cone mixers. The additive according to the invention can also be premixed with the polyvinylpyrrolidone or, for example when the additive is a liquid, eg. formic acid, can be sprayed directly onto the polyvinylpyrrolidone, after which the iodine is admixed.

In a preferred embodiment, the additive which accelerates the formation of iodide is added to an aqueous polyvinylpyrrolidone solution, for example a solution obtained by polymerization of the vinylpyrrolidone, with or without a subsequent steam distillation, before the solution is dried to produce polyvinylpyrrolidone powder, the drying being carried out by conventional methods, for example freeze-drying, drum-drying or spray-drying.

Advantageously, the polyvinylpyrrolidone is initially mixed with the additive according to the invention and the iodine at room temperature or slightly elevated temperatures of up to about 50° C., until the elementary iodine has diffused into the polyvinylpyrrolidone. The heating, to form the iodide, then takes place at 70°–100° C., and in general, the partition coefficient of about 200 which is characteristic of stable PVP-iodine, and an iodine:iodide ratio of 2:1, are achieved after from 0.5 to 9 hours, the resulting PVP-iodine having an available iodine content of from 5 to 20% by weight. These shortened heating times are a particular advantage of the process according to the invention and in addition any possible degradation of the polyvinylpyrrolidone is very substantially avoided.

The polyvinylpyrrolidone employed usually has a K value of from 8 to 50, the range from 10 to 35 being preferred. The process according to the invention is very particularly suitable for a polyvinylpyrrolidone having a K value of from 10 to 20.

A polyvinylpyrrolidone which is particularly suitable for the process according to the invention is prepared by polymerization in an organic solvent, eg. isopropanol or toluene, using an organic per-compound, eg. a dialkyl peroxide, as the source of free radicals, and may subsequently be subjected to steam distillation, as described, for example, in German Laid-Open Application DOS 2,514,127.

The amount of iodine used is as a rule from 5 to 30% by weight, preferably from 10 to 20% by weight, based on the total weight of PVP-iodine.

The Examples which follow illustrate the invention. Parts are by weight. The K values are determined in aqueous solutions by the method of H. Fikentscher, Cellulose-Chemie 13 (1932), 38-64 and 71-74. The loss of iodine is determined by keeping an aqueous PVP-iodine solution, containing 1% of available iodine, at 80° C. for 15 hours. The higher temperature of 80° C. has the advantage that the more troublesome 14 days' storage at 52° C. can be avoided and comparable values are obtained. The partition coefficient (PC) is determined in accordance with U.S. Pat. No. 3,028,300, by vigorously shaking 1.0 ml of an aqueous PVP-iodine solution having an available iodine content of 1.0% with 25 ml of heptane for one minute in a closed glass jar in a thermostatically controlled heating bath at 25.0° C. After the mixture has stood for a few minutes, the two phases are separated and the iodine content of the aqueous phase is determined by titration with sodium thiosulfate whilst the iodine content of the heptane phase is determined by spectrophotometry. The partition coefficient is calculated from the equation:

$$PC = \frac{\text{mg of iodine in the } H_2O \text{ phase}}{\text{mg of iodine in heptane}} \times \frac{\text{ml of heptane (25)}}{\text{ml of } H_2O \text{ phase (1)}}$$

The polyvinylpyrrolidone used in the Examples was prepared by the method given below, which is similar to the method in German Laid-Open Application DOS 2,514,127.

Preparation of polyvinylpyrrolidone

EXAMPLE I (K value 31.5)

160 parts of isopropanol and 80 parts of a mixture of 700 parts of vinylpyrrolidone, 140 parts of isopropanol and 3.5 parts of di-tertiary butyl peroxide are initially introduced into a stirred pressure autoclave. The mixture is then heated to 120° C., resulting in an autogenous pressure of 3 bar, and the remaining mixture is introduced into the autoclave over 3 hours. The polymerization is then continued for 3 hours, by which time the residual content of monomeric vinylpyrrolidone has fallen to below 0.5%. The mixture is then diluted with 2,500 parts of water and when it has cooled to about 80° C., the isopropanol is distilled off by introducing steam. When the material passing over has reached 98° C., the residual material is finally flushed with 700 parts of steam, and the solids content of the solution is then adjusted to 30%. The K value of the polymer is 31.5. For reactions of the solid polymer with iodine, the solid product is isolated by spray-drying.

EXAMPLE II (K value 16.6)

900 parts of a mixture of 900 parts of vinylpyrrolidone, 2,100 parts of isopropanol and 36 parts of ditertiary butyl peroxide are introduced into a stirred pressure autoclave and heated to 125° C., resulting in an autogenous pressure of 5.5 bar in the apparatus. The remaining mixture is then introduced uniformly over 3 hours and thereafter heating is continued for 1 hour, by which time the residual content of monomeric vinylpyrrolidone is less than 0.5%. The mixture is then cooled to 80° C. by releasing the pressure, resulting in the distillation of about 1,500 parts of isopropanol. The residue is then diluted with 300 parts of water and the isopropanol is distilled off completely by introducing steam. When the material passing over has reached 98° C., the residual material is finally flushed with 900 parts of steam, and the solids content of the solution is then adjusted to 40%. The K value of the polymer is 16.6. For reaction of the solid polymer with iodine, the solid product is isolated by spray-drying.

COMPARATIVE EXAMPLE: PRIOR ART METHOD WITHOUT IODIDE-FORMING ADDITIVE (A) 83 parts of PVP powder, having a K value of 31.5 and containing 2.7% of water, are mixed with 17 parts of iodine in a tumbler mixer for 1 hour at room temperature and for 2 hours at 50° C. The batch is then heated to 100° C. and at various times samples are taken and their available iodine content, partition coefficient and loss of iodine are determined. The results obtained are shown in the Table below.

TABLE 1

| Heating time at 100° C. [hours] | Available iodine content [%] | Partition coefficient | Loss of iodine after 15 hours at 80° C. [%] |
| --- | --- | --- | --- |
| 2 | 14.4 | 25 | 3.8 |
| 8 | 12.5 | 89 | 3.8 |
| 10 | 12.0 | 112 | 4.0 |
| 12 | 11.8 | 134 | 4.1 |
| 17 | 11.5 | 177 | 5.1 |
| 22 | 11.0 | 196 | 6.4 |

(B) 249 parts of PVP powder, having a K value of 16.6 and containing 1.8% of water, are mixed with 51 parts of elementary iodine in a double-cone mixer for 1 hour at room temperature and for 2 hours at 50° C. To avoid the formation of lumps, the material is then heated for 2 hours at 70° C., after which it is raised to 85° C. Higher temperatures cannot be used, as they cause lumps to form. After various times, samples are taken and the available iodine content, partition coefficient and loss of iodine are determined. The results obtained are shown in the Table below.

TABLE 2

| Heating time at 85° C. [hours] | Available iodine content [%] | Partition coefficient | Loss of iodine after 15 hours at 80° C. [%] |
| --- | --- | --- | --- |
| 15 | 12.8 | 77 | 8.8 |
| 20 | 12.0 | 99 | 9.6 |
| 35 | 11.2 | 190 | 10.2 |
| 40 | 10.9 | 199 | 11.8 |

The two Comparative Examples show that both with PVP of K value 31.5 and with PVP of K value 16.6 there is a decrease in available iodine content and an increase in the partition coefficient with increasing time of heating. From the point of view of the partition coefficients, heating for at least 17 hours is necessary, and it can be seen clearly that prolonged heating damages the product, as shown by the increasing loss of iodine. The disadvantages show particularly in the case of a PVP of low K value.

Process according to the invention

EXAMPLE 1

82.5 parts of PVP having a K value of 31.5 and containing 2.7% of water are mixed with 3.5 parts of ammonium bicarbonate for 0.5 hour in a tumbler mixer, after which 17.5 parts of elementary iodine are added and the batch is mixed for 1 hour at room temperature and 2 hours at 50° C. It is then heated for 8 hours at 100° C. Examination of the PVP-iodine obtained gives the following results:
available iodine content: 11.3%;
iodide content: 5.6%;
partition coefficient: 204;
loss of iodine: 5.3%.

EXAMPLE 2

249 parts of PVP having a K value of 31.5 and containing 2.7% of water are mixed with 3.5 parts of pulverulent crystalline oxalic acid ((COOH$_2$)$_2$.2H$_2$O) and 51 parts of elementary iodine in a tumbler mixer for 2 hours at room temperature and 2 hours at 50° C. The batch is then heated for 7 hours at 100° C. Examination of the PVP-iodine obtained gives the following results:
available iodine content: 11.1%;
partition coefficient: 205;
loss of iodine: 3.8%.

EXAMPLE 3

2.7 parts of 98% strength formic acid are sprayed slowly and extremely finely, from a nozzle, onto 249 parts of PVP having a K value of 16.6 and containing 1.8% of water, in a tumbler mixer, with the mixer running. After mixing the batch for 1 hour, 51 parts of elementary iodine are added. The batch is then mixed for 1 hour at room temperature and 2 hours at 50° C., after which it is heated for 2 hours at 70° C. and 6 hours at 85° C. Examination of the PVP-iodine obtained gives the following results:
available iodine content: 10.2%;
partition coefficient: 197;
loss of iodine: 10.5%.

EXAMPLE 4

3.75 parts of 98% strength formic acid are mixed into 1,000 parts of a 30% strength aqueous solution of a polyvinylpyrrolidone having a K value of 31.5 and the pH of the solution is brought to 7.2 and 6.2 parts of aqueous ammonia of about 25% strength. The solution is sprayed in a spray-dryer, with the air entering at 160° C. and leaving at 100° C. The dried product obtained contains 2.4% of water and a total of 1.1% of formic acid, of which 0.9% is in the free form and 0.2% in the form of the ammonium salt.

249 parts of the PVP containing formic acid are then mixed with 51 parts of elementary iodine in a tumbler mixer for 1 hour at room temperature and 2 hours at 50° C., after which the batch is heated for 4 hours at 100° C. Examination of the PVP-iodine obtained gives the following results:
available iodine content: 11.4%;
partition coefficient: 198;
loss of iodine: 3.7%.

EXAMPLE 5

4 parts of 98% strength formic acid are mixed into 500 parts of a 40% strength aqueous solution of a polyvinylpyrrolidone having a K value of 16.6. The solution is sprayed in a spray-dryer, with the air entering at 140° C. and leaving at 80° C. The dried product contains 1.9% of water and 1.2% of formic acid.

124.5 parts of the PVP containing formic acid are mixed with 25.5 parts of elementary iodine for 1 hour at room temperature and for 2 hours at 50° C., and the batch is then heated for 2 hours at 70° C. and 6 hours at 85° C. Examination of the PVP-iodine obtained gives the following results:
available iodine content: 11.1%;
partition coefficient: 207;
loss of iodine: 9.8%.

EXAMPLE 6

667 parts of a 30% strength aqueous solution of polyvinylpyrrolidone having a K value 31.5 are mixed with 5 parts of formamide. The solution is sprayed in a spray-dryer, with the air entering at 160° C. and leaving at 100° C. The dried product contains 3.2% of water and 1.2% of formamide. 124.5 parts of this polyvinylpyrrolidone are mixed with 25.5 parts of elementary iodine for 1 hour at room temperature and for 2 hours at 50° C.

and the batch is then heated for 4 hours at 100° C. Examination of the PVP-iodine obtained gives the following results:

available iodine content: 11.5%;
partition coefficient: 201;
loss of iodine: 3.0%.

We claim:

1. A process for the preparation of PVP-iodine by reacting polyvinylpyrrolidone powder with elementary iodine at from 70° to 100° C., wherein the reaction is carried out in the presence of formic acid, oxalic acid or an ammonium salt or amide of carbonic acid, formic acid or oxalic acid.

2. A process as claimed in claim 1, wherein the reaction is carried out in the presence of formic acid or oxalic acid, their ammonium salts or their amides.

3. A process as claimed in claim 1, wherein the additive which accelerates the formation of iodide is added to an aqueous polyvinylpyrrolidone solution and the latter is then dried.

4. A process as claimed in claim 1, wherein a polyvinylpyrrolidone having a K value of from 10 to 35 is reacted.

* * * * *